(12) United States Patent
Kikly et al.

(10) Patent No.: US 12,037,387 B2
(45) Date of Patent: Jul. 16, 2024

(54) PAN-ELR+ CXC CHEMOKINE ANTIBODIES FOR THE TREATMENT OF HIDRADENITIS SUPPURATIVA

(71) Applicant: Eli Lilly and Company, Indianapolis, IN (US)

(72) Inventors: Kristine Kay Kikly, Spiceland, IN (US); Dipak Ratilal Patel, San Diego, CA (US); Derrick Ryan Witcher, Fishers, IN (US)

(73) Assignee: ELI LILLY AND COMPANY, Indianapolis, IN (US)

( * ) Notice: Subject to any disclaimer, the term of this patent is extended or adjusted under 35 U.S.C. 154(b) by 727 days.

(21) Appl. No.: 17/284,611

(22) PCT Filed: Oct. 15, 2019

(86) PCT No.: PCT/US2019/056250
§ 371 (c)(1),
(2) Date: Apr. 12, 2021

(87) PCT Pub. No.: WO2020/086327
PCT Pub. Date: Apr. 30, 2020

(65) Prior Publication Data
US 2021/0340244 A1  Nov. 4, 2021

Related U.S. Application Data

(60) Provisional application No. 62/791,061, filed on Jan. 11, 2019, provisional application No. 62/748,838, filed on Oct. 22, 2018.

(51) Int. Cl.
| | |
|---|---|
| C07K 16/24 | (2006.01) |
| A61K 9/00 | (2006.01) |
| A61P 17/00 | (2006.01) |
| A61K 39/00 | (2006.01) |

(52) U.S. Cl.
CPC ............ C07K 16/24 (2013.01); A61K 9/0019 (2013.01); A61P 17/00 (2018.01); *A61K 2039/505* (2013.01); *A61K 2039/54* (2013.01); *A61K 2039/545* (2013.01); *C07K 2317/33* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | | |
|---|---|---|---|---|
| 9,290,570 B2 * | 3/2016 | Beidler | ................... | C07K 16/24 |
| 9,783,605 B2 * | 10/2017 | Beidler | ................ | C07K 16/244 |
| 10,093,727 B2 * | 10/2018 | Beidler | ................... | C07K 16/24 |
| 10,858,425 B2 * | 12/2020 | Beidler | .............. | A61K 39/3955 |
| 2017/0349898 A1 * | 12/2017 | Dalla | ........................ | C12N 7/00 |

FOREIGN PATENT DOCUMENTS

| | | | | |
|---|---|---|---|---|
| WO | 2014/149733 A1 | 9/2014 | | |
| WO | WO-2014149733 A1 * | 9/2014 | ................ | A61P 1/00 |
| WO | WO-2016098071 A1 * | 6/2016 | .............. | A61P 29/00 |
| WO | 2018/150265 A1 | 8/2018 | | |

OTHER PUBLICATIONS

Gorovoy, et al., "Successful Treatment of Recalcitrant Hidradenitis Suppurativa with Adalimumab", Case Reports in Dermatology, vol. 1, No. 1, Jan. 1, 2009 (Jan. 1, 2009), pp. 71-77.
Blok, et al., "Ustekinumab in hidradenitis suppurativa: clinical results and a search for potential biomarkers in serum", British Journal of Dermatology, vol. 174, No. 4, Apr. 1, 2016 (Apr. 1, 2016), pp. 839-846.
Vossen, et al., "Novel cytokine and chemokine markers of hidradenitis suppurativa reflect chronic inflammation and itch", Allergy, Dec. 10, 2018 (Dec. 10, 2018).
Vossen, et al., "Hidradenitis Suppurativa: A Systematic Review Integrating Inflammatory Pathways Into a Cohesive Pathogenic Model", Frontiers In Immunology, vol. 9, Dec. 14, 2018 (Dec. 14, 2018).
International Search Report for PCT/US2019/056250, dated Jan. 21, 2020.
Written Opinion of the International Searching Authority for PCT/US2019/056250, dated Jan. 21, 2020.
ClinicalTrials.gov Identifier: NCT04493502, Jul. 29, 2020.
ClinicalTrials.gov Identifier: NCT02896868, Oct. 3, 2018.

* cited by examiner

*Primary Examiner* — Laura B Goddard
(74) *Attorney, Agent, or Firm* — Dipa Patel

(57) ABSTRACT

Provided herein are methods and uses of antibodies against ELR+ CXC chemokines for the treatment of hidradenitis suppurativa. Also provided are doses and dosing regimens for the methods and uses of antibodies against ELR+ CXC chemokines for the treatment of hidradenitis suppurativa.

22 Claims, No Drawings

Specification includes a Sequence Listing.

SEQUENCE LISTING

<160> NUMBER OF SEQ ID NOS: 19

<210> SEQ ID NO 1
<211> LENGTH: 452
<212> TYPE: PRT
<213> ORGANISM: Artificial Sequence
<220> FEATURE:
<223> OTHER INFORMATION: synthetic construct -continued

<400> SEQUENCE: 1

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Glu Phe Thr Ser Tyr
            20                  25                  30

Trp Ile His Trp Val Arg Gln Ala Pro Gly Gln Gly Leu Glu Trp Met
        35                  40                  45

Gly Asn Ile Ser Pro Asn Ser Gly Ser Ala Asn Tyr Asn Glu Lys Phe
    50                  55                  60

Lys Ser Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Gly Pro Tyr Ser Tyr Tyr Pro Ser Arg Glu Tyr Tyr Gly
            100                 105                 110

Ser Asp Leu Trp Gly Gln Gly Thr Leu Val Thr Val Ser Ser Ala Ser
        115                 120                 125

Thr Lys Gly Pro Ser Val Phe Pro Leu Ala Pro Cys Ser Arg Ser Thr
    130                 135                 140

Ser Glu Ser Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Lys Thr Tyr Thr
        195                 200                 205

Cys Asn Val Asp His Lys Pro Ser Asn Thr Lys Val Asp Lys Arg Val
    210                 215                 220

Glu Ser Lys Tyr Gly Pro Pro Cys Pro Pro Cys Pro Ala Pro Glu Phe
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser Gln Glu Asp Pro Glu Val Gln Phe Asn Trp Tyr Val Asp Gly Val
        275                 280                 285

Glu Val His Asn Ala Lys Thr Lys Pro Arg Glu Glu Gln Phe Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Gly Leu Pro Ser
                325                 330                 335

Ser Ile Glu Lys Thr Ile Ser Lys Ala Lys Gly Gln Pro Arg Glu Pro
            340                 345                 350

Gln Val Tyr Thr Leu Pro Pro Ser Gln Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Arg Leu

```
                    405                 410                 415
Thr Val Asp Lys Ser Arg Trp Gln Glu Gly Asn Val Phe Ser Cys Ser
            420                 425                 430

Val Met His Glu Ala Leu His Asn His Tyr Thr Gln Lys Ser Leu Ser
            435                 440                 445

Leu Ser Leu Gly
        450

<210> SEQ ID NO 2
<211> LENGTH: 126
<212> TYPE: PRT
<213> ORGANISM: Artificial Sequence
<220> FEATURE:
<223> OTHER INFORMATION: synthetic construct

<400> SEQUENCE: 2

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Glu Phe Thr Ser Tyr
            20                  25                  30

Trp Ile His Trp Val Arg Gln Ala Pro Gly Gln Gly Leu Glu Trp Met
        35                  40                  45

Gly Asn Ile Ser Pro Asn Ser Gly Ser Ala Asn Tyr Asn Glu Lys Phe
    50                  55                  60

Lys Ser Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Gly Pro Tyr Ser Tyr Tyr Pro Ser Arg Glu Tyr Tyr Gly
            100                 105                 110

Ser Asp Leu Trp Gly Gln Gly Thr Leu Val Thr Val Ser Ser
        115                 120                 125

<210> SEQ ID NO 3
<211> LENGTH: 214
<212> TYPE: PRT
<213> ORGANISM: Artificial Sequence
<220> FEATURE:
<223> OTHER INFORMATION: synthetic construct

<400> SEQUENCE: 3

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Asn Asn
            20                  25                  30

Leu His Trp Tyr Gln Gln Lys Pro Gly Gln Ala Pro Arg Leu Leu Ile
        35                  40                  45

Tyr Tyr Thr Ser Arg Ser Val Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gly Gln Asn Asn Glu Trp Pro Glu
                85                  90                  95

Val Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125
```

```
Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 4
<211> LENGTH: 107
<212> TYPE: PRT
<213> ORGANISM: Artificial Sequence
<220> FEATURE:
<223> OTHER INFORMATION: synthetic construct

<400> SEQUENCE: 4

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Asn Asn
            20                  25                  30

Leu His Trp Tyr Gln Gln Lys Pro Gly Gln Ala Pro Arg Leu Leu Ile
        35                  40                  45

Tyr Tyr Thr Ser Arg Ser Val Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gly Gln Asn Asn Glu Trp Pro Glu
                85                  90                  95

Val Phe Gly Gly Gly Thr Lys Val Glu Ile Lys
            100                 105

<210> SEQ ID NO 5
<211> LENGTH: 1356
<212> TYPE: DNA
<213> ORGANISM: Artificial Sequence
<220> FEATURE:
<223> OTHER INFORMATION: synthetic construct

<400> SEQUENCE: 5
caggtgcagc tggtgcagtc tggtgctgaa gtgaagaagc ctggggcctc agtgaaggtg      60
tcctgcaagg catctggcta cgagttcacc agctactgga ttcactgggt gcgacaggcc     120
cctggacaag gcttgagtg gatgggaaat atttctccta atagtggtag tgctaactac     180
aatgagaagt tcaagagcag agtcaccatg accaggaca cgtccacgag cacagtctac     240
atggagctga gcagcctgag atctgaggac acggccgtgt attactgtgc gagagagggc     300
ccttacagtt attatccgag tagggagtac tatggctctg acctctgggg gcaagggacc     360
ctagtcacag tctcctcagc ctccaccaag ggcccatcgg tcttccccct ggcgccctgc     420
tccaggagca cctccgagag cacagccgcc ctgggctgcc tggtcaagga ctacttcccc     480
gaaccggtga cggtgtcgtg gaactcaggc gccctgacca gcggcgtgca caccttcccg     540
gctgtcctac agtcctcagg actctactcc ctcagcagcg tggtgaccgt gccctccagc     600
```

```
agcttgggca cgaagaccta cacctgcaac gtagatcaca agcccagcaa caccaaggtg    660
gacaagagag ttgagtccaa atatggtccc ccatgcccac cctgcccagc acctgagttc    720
ctggggggac catcagtctt cctgttcccc ccaaaaccca aggacactct catgatctcc    780
cggacccctg aggtcacgtg cgtggtggtg gacgtgagcc aggaagaccc cgaggtccag    840
ttcaactggt acgtggatgg cgtggaggtg cataatgcca agacaaagcc gcgggaggag    900
cagttcaaca gcacgtaccg tgtggtcagc gtcctcaccg tcctgcacca ggactggctg    960
aacggcaagg agtacaagtg caaggtctcc aacaaaggcc tcccgtcctc catcgagaaa   1020
accatctcca agccaaagg gcagccccga gagccacagg tgtacaccct gcccccatcc   1080
caggaggaga tgaccaagaa ccaggtcagc ctgacctgcc tggtcaaagg cttctacccc   1140
agcgacatcg ccgtggagtg ggaaagcaat gggcagccgg agaacaacta caagaccacg   1200
cctcccgtgc tggactccga cggctccttc ttcctctaca gcaggctaac cgtggacaag   1260
agcaggtggc aggaggggaa tgtcttctca tgctccgtga tgcatgaggc tctgcacaac   1320
cactacacac agaagagcct ctccctgtct ctgggt                             1356

<210> SEQ ID NO 6
<211> LENGTH: 642
<212> TYPE: DNA
<213> ORGANISM: Artificial Sequence
<220> FEATURE:
<223> OTHER INFORMATION: synthetic construct

<400> SEQUENCE: 6
gaaattgtgt tgacacagtc tccagccacc ctgtctttgt ctccagggga aagagccacc     60
ctctcctgca gggccagtca agtatcagc aataacctac actggtacca acagaaacct    120
ggccaggctc ccaggctcct catctattat acttcccggt ccgtctctgg catcccagcc    180
aggttcagtg gcagtgggtc tgggacagac ttcactctca ccatcagcag cctagagcct    240
gaagattttg cagtttatta ctgtggacag aataacgagt ggcctgaggt gttcggcgga    300
gggaccaagg tggagatcaa acgaactgtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gc                      642

<210> SEQ ID NO 7
<211> LENGTH: 11
<212> TYPE: PRT
<213> ORGANISM: Artificial Sequence
<220> FEATURE:
<223> OTHER INFORMATION: synthetic construct

<400> SEQUENCE: 7

Arg Ala Ser Gln Ser Ile Ser Asn Asn Leu His
1               5                   10

<210> SEQ ID NO 8
<211> LENGTH: 7
<212> TYPE: PRT
<213> ORGANISM: Artificial Sequence
<220> FEATURE:
<223> OTHER INFORMATION: synthetic construct
```

```
<400> SEQUENCE: 8

Tyr Thr Ser Arg Ser Val Ser
1               5

<210> SEQ ID NO 9
<211> LENGTH: 9
<212> TYPE: PRT
<213> ORGANISM: Artificial Sequence
<220> FEATURE:
<223> OTHER INFORMATION: synthetic construct

<400> SEQUENCE: 9

Gly Gln Asn Asn Glu Trp Pro Glu Val
1               5

<210> SEQ ID NO 10
<211> LENGTH: 10
<212> TYPE: PRT
<213> ORGANISM: Artificial Sequence
<220> FEATURE:
<223> OTHER INFORMATION: synthetic construct

<400> SEQUENCE: 10

Gly Tyr Glu Phe Thr Ser Tyr Trp Ile His
1               5                   10

<210> SEQ ID NO 11
<211> LENGTH: 17
<212> TYPE: PRT
<213> ORGANISM: Artificial Sequence
<220> FEATURE:
<223> OTHER INFORMATION: synthetic construct

<400> SEQUENCE: 11

Asn Ile Ser Pro Asn Ser Gly Ser Ala Asn Tyr Asn Glu Lys Phe Lys
1               5                   10                  15

Ser

<210> SEQ ID NO 12
<211> LENGTH: 17
<212> TYPE: PRT
<213> ORGANISM: Artificial Sequence
<220> FEATURE:
<223> OTHER INFORMATION: synthetic construct

<400> SEQUENCE: 12

Glu Gly Pro Tyr Ser Tyr Tyr Pro Ser Arg Glu Tyr Tyr Gly Ser Asp
1               5                   10                  15

Leu

<210> SEQ ID NO 13
<211> LENGTH: 73
<212> TYPE: PRT
<213> ORGANISM: Homo sapiens

<400> SEQUENCE: 13

Ala Ser Val Ala Thr Glu Leu Arg Cys Gln Cys Leu Gln Thr Leu Gln
1               5                   10                  15

Gly Ile His Pro Lys Asn Ile Gln Ser Val Asn Val Lys Ser Pro Gly
                20                  25                  30

Pro His Cys Ala Gln Thr Glu Val Ile Ala Thr Leu Lys Asn Gly Arg
            35                  40                  45

Lys Ala Cys Leu Asn Pro Ala Ser Pro Ile Val Lys Lys Ile Ile Glu
```

```
                50                  55                  60
Lys Met Leu Asn Ser Asp Lys Ser Asn
 65                  70
```

<210> SEQ ID NO 14
<211> LENGTH: 73
<212> TYPE: PRT
<213> ORGANISM: Homo sapiens

<400> SEQUENCE: 14

```
Ala Pro Leu Ala Thr Glu Leu Arg Cys Gln Cys Leu Gln Thr Leu Gln
 1               5                  10                  15
Gly Ile His Leu Lys Asn Ile Gln Ser Val Lys Val Lys Ser Pro Gly
                20                  25                  30
Pro His Cys Ala Gln Thr Glu Val Ile Ala Thr Leu Lys Asn Gly Gln
            35                  40                  45
Lys Ala Cys Leu Asn Pro Ala Ser Pro Met Val Lys Lys Ile Ile Glu
        50                  55                  60
Lys Met Leu Lys Asn Gly Lys Ser Asn
 65                  70
```

<210> SEQ ID NO 15
<211> LENGTH: 73
<212> TYPE: PRT
<213> ORGANISM: Homo sapiens

<400> SEQUENCE: 15

```
Ala Ser Val Val Thr Glu Leu Arg Cys Gln Cys Leu Gln Thr Leu Gln
 1               5                  10                  15
Gly Ile His Leu Lys Asn Ile Gln Ser Val Asn Val Arg Ser Pro Gly
                20                  25                  30
Pro His Cys Ala Gln Thr Glu Val Ile Ala Thr Leu Lys Asn Gly Lys
            35                  40                  45
Lys Ala Cys Leu Asn Pro Ala Ser Pro Met Val Gln Lys Ile Ile Glu
        50                  55                  60
Lys Ile Leu Asn Lys Gly Ser Thr Asn
 65                  70
```

<210> SEQ ID NO 16
<211> LENGTH: 74
<212> TYPE: PRT
<213> ORGANISM: Homo sapiens

<400> SEQUENCE: 16

```
Ala Ala Val Leu Arg Glu Leu Arg Cys Val Cys Leu Gln Thr Thr Gln
 1               5                  10                  15
Gly Val His Pro Lys Met Ile Ser Asn Leu Gln Val Phe Ala Ile Gly
                20                  25                  30
Pro Gln Cys Ser Lys Val Glu Val Val Ala Ser Leu Lys Asn Gly Lys
            35                  40                  45
Glu Ile Cys Leu Asp Pro Glu Ala Pro Phe Leu Lys Lys Val Ile Gln
        50                  55                  60
Lys Ile Leu Asp Gly Gly Asn Lys Glu Asn
 65                  70
```

<210> SEQ ID NO 17
<211> LENGTH: 75
<212> TYPE: PRT
<213> ORGANISM: Homo sapiens

```
<400> SEQUENCE: 17

Val Ser Ala Val Leu Thr Glu Leu Arg Cys Thr Cys Leu Arg Val Thr
1               5                   10                  15

Leu Arg Val Asn Pro Lys Thr Ile Gly Lys Leu Gln Val Phe Pro Ala
            20                  25                  30

Gly Pro Gln Cys Ser Lys Val Glu Val Val Ala Ser Leu Lys Asn Gly
        35                  40                  45

Lys Gln Val Cys Leu Asp Pro Glu Ala Pro Phe Leu Lys Lys Val Ile
    50                  55                  60

Gln Lys Ile Leu Asp Ser Gly Asn Lys Lys Asn
65                  70                  75

<210> SEQ ID NO 18
<211> LENGTH: 70
<212> TYPE: PRT
<213> ORGANISM: Homo sapiens

<400> SEQUENCE: 18

Ala Glu Leu Arg Cys Met Cys Ile Lys Thr Thr Ser Gly Ile His Pro
1               5                   10                  15

Lys Asn Ile Gln Ser Leu Glu Val Ile Gly Lys Gly Thr His Cys Asn
            20                  25                  30

Gln Val Glu Val Ile Ala Thr Leu Lys Asp Gly Arg Lys Ile Cys Leu
        35                  40                  45

Asp Pro Asp Ala Pro Arg Ile Lys Lys Ile Val Gln Lys Lys Leu Ala
    50                  55                  60

Gly Asp Glu Ser Ala Asp
65                  70

<210> SEQ ID NO 19
<211> LENGTH: 72
<212> TYPE: PRT
<213> ORGANISM: Homo sapiens

<400> SEQUENCE: 19

Ser Ala Lys Glu Leu Arg Cys Gln Cys Ile Lys Thr Tyr Ser Lys Pro
1               5                   10                  15

Phe His Pro Lys Phe Ile Lys Glu Leu Arg Val Ile Glu Ser Gly Pro
            20                  25                  30

His Cys Ala Asn Thr Glu Ile Ile Val Lys Leu Ser Asp Gly Arg Glu
        35                  40                  45

Leu Cys Leu Asp Pro Lys Glu Asn Trp Val Gln Arg Val Val Glu Lys
    50                  55                  60

Phe Leu Lys Arg Ala Glu Asn Ser
65                  70
```

PAN-ELR+ CXC CHEMOKINE ANTIBODIES FOR THE TREATMENT OF HIDRADENITIS SUPPURATIVA

The present invention relates to methods and uses of antibodies against ELR+ CXC chemokines for the treatment of hidradenitis suppurativa. The present invention also relates to doses and dosing regimens for the methods and uses of antibodies against ELR+ CXC chemokines for the treatment of hidradenitis suppurativa.

ELR+ CXC chemokines (so-called because members of the chemokine family all possess an E-L-R amino acid motif immediately adjacent to their CXC motif) play an important role in a variety of pathogenic mechanisms, including the migration of neutrophils to sites of inflammation and angiogenesis. Neutrophils contribute to the pathogenesis of several acute and chronic inflammatory and autoimmune diseases.

Chemokines are grouped into four subfamilies: CXC, CC, (X)C, and CX3C. In the CXC chemokines, one amino acid separates the first two cysteines ("the CXC motif"). ELR+ CXC chemokines are ligands for CXCR1 and/or CXCR2 chemokine receptors, which are G-protein coupled seven transmembrane domain-type receptors that specifically bind ELR+ CXC chemokines. The seven human ELR+ CXC chemokines are human growth-regulated oncogene ("Gro")-alpha (also known as CXCL1), human Gro-beta (also known as CXCL2), human Gro-gamma (also known as CXCL3), human ENA-78 (also known as CXCL5 or human epithelial neutrophil activating peptide-78), human GCP-2 (also known as CXCL6 or human granulocyte chemotactic protein-2), human NAP-2 (also known as CXCL7 or human neutrophil activating protein-2), and human IL-8 (also known as CXCL8 or human interleukin-8). All ELR+ CXC chemokines bind the CXCR2 receptor; moreover, some ELR+ CXC chemokines bind both CXCR1 and CXCR2 receptors (i.e., CXCL6 and CXCL8), all of which contributes to redundancy in the activation pathways. Neutralizing all seven ELR+ CXC chemokines could impact the ability of CXCR1+ or CXCR2+ cells to migrate to sites of inflammation.

Antibodies that bind and neutralize all seven human ELR+ CXC chemokines have been previously described, e.g., in WO 2014149733, EP 2970447B1, U.S. Pat. No. 9,290,570. Given their ability to bind and neutralize all seven human ELR+ CXC chemokines, those antibodies offer advantages over monotherapies targeting single human ELR+ CXC chemokines and combination therapies targeting multiple human ELR+ CXC chemokines. One of such antibodies that bind all seven human ELR+ CXC chemokines is Antibody 1 that comprises light chain complementarity determining regions ("LCDR") LCDR1, LCDR2, LCDR3, and heavy chain complementarity determining regions ("HCDR") HCDR1, HCDR2, HCDR3, wherein LCDR1 comprises SEQ ID NO: 7, LCDR2 comprises SEQ ID NO: 8, LCDR3 comprises SEQ ID NO: 9, HCDR1 comprises SEQ ID NO: 10, HCDR2 comprises SEQ ID NO: 11, and HCDR3 comprises SEQ ID NO: 12. Antibody 1 comprises a heavy chain variable region comprising the amino acid sequence of SEQ ID NO: 2 and a light chain variable region comprising the amino acid sequence of SEQ ID NO: 4. Antibody 1 comprises a heavy chain having the amino acid sequence of SEQ ID NO: 1 and a light chain having the amino acid sequence of SEQ ID NO: 3. It was shown that Antibody 1 binds an epitope that is common to all seven human ELR+ CXC chemokines and neutralize the activities of all seven human ELR+ CXC chemokines. By binding to all seven ELR+ CXC chemokines, both the CXCR1 and the CXCR2 pathways can be blocked, which may result in more effective inhibition of neutrophil trafficking.

Hidradenitis suppurativa (HS) is a chronic, recurrent, inflammatory disease, which is associated with substantial co-morbidities and decreased quality of life. HS initially presents as tender subcutaneous nodules. These lesions may spontaneously rupture or coalesce to form deep dermal painful abscesses, and they often exude a purulent drainage. The inflammatory abscesses ultimately heal, producing fibrosis, dermal contractures, and induration of the skin. HS typically occurs after puberty, with average age of onset in the second or third decades of life; women are more likely to develop this disease.

It is now considered that HS lesions begin with follicular plugging which presumably results in occlusion and dilation of the pilosebaceous unit, with subsequent rupture (Alikhan et al., Hidradenitis suppurativa: a comprehensive review. *J Am Acad Dermatol.* 2009; 60(4):539-561). Extrusion of follicular contents (primarily consisting of corneocytes, bacteria, sebum products, and hair in the dermis) produces a chemotactic inflammatory response. The resulting influx of neutrophils, lymphocytes, and histiocytes lead to abscess formation.

There is no uniformly effective single therapy for HS resulting in numerous treatment modalities being employed. These include antibiotics, retinoids, hormones, immunosuppressive and anti-inflammatory agents, neurotoxins, radiotherapy, and surgery. The tumor necrosis factor inhibitor, adalimumab, was approved for the treatment of HS in 2015. However, many HS patients do not respond to adalimumab. There remains a substantial unmet medical need for effective therapies for treating HS.

Additionally, there is no prior description of any safe, tolerable and effective use of an antibody that binds and neutralizes all seven human ELR+ CXC chemokines in human patients.

Provided herein are methods of treating hidradenitis suppurativa in a human patient in need thereof by administering to the human patient a therapeutically effective amount of an antibody that binds all seven human ELR+ CXC chemokines, e.g., Antibody 1, or a pharmaceutical composition comprising such an antibody. In some embodiments, provided herein are methods of treating hidradenitis suppurativa in a human patient in need thereof comprising administering to the human patient a therapeutically effective amount of an antibody that binds human growth-regulated oncogene ("Gro")-alpha, human Gro-beta, human Gro-gamma, human epithelial neutrophil activating peptide-78, human granulocyte chemotactic protein-2, human neutrophil activating protein-2, and human interleukin-8, or a pharmaceutical composition comprising such an antibody, wherein the antibody comprises light chain complementarity determining regions ("LCDR") LCDR1, LCDR2, LCDR3, and heavy chain complementarity determining regions ("HCDR") HCDR1, HCDR2, HCDR3, wherein LCDR1 comprises SEQ ID NO: 7, LCDR2 comprises SEQ ID NO: 8, LCDR3 comprises SEQ ID NO: 9, HCDR1 comprises SEQ ID NO: 10, HCDR2 comprises SEQ ID NO: 11, and HCDR3 comprises SEQ ID NO: 12. In some embodiments, the antibody comprises a heavy chain variable region comprising the amino acid sequence of SEQ ID NO: 2 and a light chain variable region comprising the amino acid sequence of SEQ ID NO: 4. In some embodiments, the antibody comprises a heavy chain having the amino acid sequence of SEQ ID NO: 1 and a light chain having the amino acid sequence of SEQ ID NO: 3.

Also provided herein are antibodies that bind all seven human ELR+ CXC chemokines, e.g., Antibody 1, or a pharmaceutical composition comprising such an antibody, for use in the treatment of hidradenitis suppurativa. In some embodiments, provided herein is an antibody that binds human growth-regulated oncogene ("Gro")-alpha, human Gro-beta, human Gro-gamma, human epithelial neutrophil activating peptide-78, human granulocyte chemotactic protein-2, human neutrophil activating protein-2, and human interleukin-8, wherein the antibody comprises light chain complementarity determining regions ("LCDR") LCDR1, LCDR2, LCDR3 and heavy chain complementarity determining regions ("HCDR") HCDR1, HCDR2, HCDR3, wherein LCDR1 comprises SEQ ID NO: 7, LCDR2 comprises SEQ ID NO: 8, LCDR3 comprises SEQ ID NO: 9, HCDR1 comprises SEQ ID NO: 10, HCDR2 comprises SEQ ID NO: 11, and HCDR3 comprises SEQ ID NO: 12, or a pharmaceutical composition comprising such an antibody, for use in the treatment of hidradenitis suppurativa. In some embodiments, the antibody comprises a heavy chain variable region comprising the amino acid sequence of SEQ ID NO: 2 and a light chain variable region comprising the amino acid sequence of SEQ ID NO: 4. In some embodiments, the antibody comprises a heavy chain having the amino acid sequence of SEQ ID NO: 1 and a light chain having the amino acid sequence of SEQ ID NO: 3.

Also provided herein are uses of antibodies that bind all seven human ELR+ CXC chemokines, e.g., Antibody 1, in the manufacture of a medicament for the treatment of hidradenitis suppurativa. In some embodiments, provided herein is use of an antibody that binds human growth-regulated oncogene ("Gro")-alpha, human Gro-beta, human Gro-gamma, human epithelial neutrophil activating peptide-78, human granulocyte chemotactic protein-2, human neutrophil activating protein-2, and human interleukin-8, wherein the antibody comprises light chain complementarity determining regions ("LCDR") LCDR1, LCDR2, LCDR3 and heavy chain complementarity determining regions ("HCDR") HCDR1, HCDR2, HCDR3, wherein LCDR1 comprises SEQ ID NO: 7, LCDR2 comprises SEQ ID NO: 8, LCDR3 comprises SEQ ID NO: 9, HCDR1 comprises SEQ ID NO: 10, HCDR2 comprises SEQ ID NO: 11, and HCDR3 comprises SEQ ID NO: 12, in the manufacture of a medicament for the treatment of hidradenitis suppurativa. In some embodiments, the antibody comprises a heavy chain variable region comprising the amino acid sequence of SEQ ID NO: 2 and a light chain variable region comprising the amino acid sequence of SEQ ID NO: 4. In some embodiments, the antibody comprises a heavy chain having the amino acid sequence of SEQ ID NO: 1 and a light chain having the amino acid sequence of SEQ ID NO: 3.

In some embodiments, the antibody that binds all seven human ELR+ CXC chemokines, e.g., Antibody 1, or a pharmaceutical composition comprising such an antibody, is administered intravenously. In some embodiments, the antibody that binds all seven human ELR+ CXC chemokines, e.g., Antibody 1, or a pharmaceutical composition comprising such an antibody, is administered subcutaneously.

As discussed below, the terminal half-life (t½) for Antibody 1 is estimated to be about 2 weeks. In some embodiments, the antibody that binds all seven human ELR+ CXC chemokines, e.g., Antibody 1, or a pharmaceutical composition comprising such an antibody, is administered once every two weeks. In some embodiments, the antibody that binds all seven human ELR+ CXC chemokines, e.g., Antibody 1, or a pharmaceutical composition comprising such an antibody, is administered weekly.

In some embodiments, the antibody that binds all seven human ELR+ CXC chemokines, e.g., Antibody 1, or a pharmaceutical composition comprising such an antibody, is administered intravenously at a dose of about 100 mg to about 1000 mg (e.g., about 100 mg to about 1000 mg, about 150 mg to about 900 mg, about 200 mg to about 800 mg, about 250 mg to about 700 mg, about 300 mg to about 600 mg, about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 850 mg, about 900 mg, about 950 mg, about 1000 mg).

In some embodiments, the antibody that binds all seven human ELR+ CXC chemokines, e.g., Antibody 1, or a pharmaceutical composition comprising such an antibody, is administered intravenously at a dose of about 100 mg to about 600 mg (e.g., about 100 mg to about 600 mg, about 200 mg to about 600 mg, about 300 mg to about 600 mg, about 400 mg to about 600 mg, about 500 mg to about 600 mg, about 100 mg to about 500 mg, about 200 mg to about 500 mg, about 300 mg to about 500 mg, about 400 mg to about 500 mg, about 100 mg to about 400 mg, about 200 mg to about 400 mg, about 300 mg to about 400 mg, about 100 mg to about 300 mg, about 200 mg to about 300 mg, about 100 mg to about 200 mg, about 100 mg, about 150 mg, about 200 mg, about 250 mg, about 300 mg, about 350 mg, about 400 mg, about 450 mg, about 500 mg, about 550 mg, about 600 mg).

In some embodiments, the antibody that binds all seven human ELR+ CXC chemokines, e.g., Antibody 1, or a pharmaceutical composition comprising such an antibody, is administered at a dose of about 100 mg to about 600 mg (e.g., about 100 mg to about 600 mg, about 200 mg to about 600 mg, about 300 mg to about 600 mg, about 400 mg to about 600 mg, about 500 mg to about 600 mg, about 100 mg to about 500 mg, about 200 mg to about 500 mg, about 300 mg to about 500 mg, about 400 mg to about 500 mg, about 100 mg to about 400 mg, about 200 mg to about 400 mg, about 300 mg to about 400 mg, about 100 mg to about 300 mg, about 200 mg to about 300 mg, about 100 mg to about 200 mg, about 100 mg, about 150 mg, about 200 mg, about 250 mg, about 300 mg, about 350 mg, about 400 mg, about 450 mg, about 500 mg, about 550 mg, about 600 mg) once every two weeks intravenously.

In some embodiments, the antibody that binds all seven human ELR+ CXC chemokines, e.g., Antibody 1, or a pharmaceutical composition comprising such an antibody, is administered at a dose of about 600 mg to about 1000 mg (e.g., about 600 mg to about 1000 mg, about 650 mg to about 950 mg, about 700 mg to about 900 mg, about 750 mg to about 850 mg, about 600 mg, about 650 mg, about 700 mg, about 750 mg, about 800 mg, about 850 mg, about 900 mg, about 950 mg, about 100 mg) once every two weeks intravenously.

In some embodiments, the antibody that binds all seven human ELR+ CXC chemokines, e.g., Antibody 1, or a pharmaceutical composition comprising such an antibody, is administered at a dose of about 200 mg to about 600 mg (e.g., about 200 mg, about 250 mg, about 300 mg, about 350 mg, about 400 mg, about 450 mg, about 500 mg, about 550 mg, about 600 mg) once every two weeks intravenously.

In some embodiments, the antibody that binds all seven human ELR+ CXC chemokines, e.g., Antibody 1, or a pharmaceutical composition comprising such an antibody, is administered at a dose of about 300 mg to about 600 mg (e.g., about 300 mg, about 350 mg, about 400 mg, about 450 mg, about 500 mg, about 550 mg, about 600 mg) once every two weeks intravenously.

In some embodiments, the antibody that binds all seven human ELR+ CXC chemokines, e.g., Antibody 1, or a pharmaceutical composition comprising such an antibody, is administered at a dose of about 100 mg to about 150 mg once every two weeks intravenously.

In some embodiments, the antibody that binds all seven human ELR+ CXC chemokines, e.g., Antibody 1, or a pharmaceutical composition comprising such an antibody, is administered at a dose of about 300 mg once every two weeks intravenously.

In some embodiments, the antibody that binds all seven human ELR+ CXC chemokines, e.g., Antibody 1, or a pharmaceutical composition comprising such an antibody, is administered at a dose of about 600 mg once every two weeks intravenously.

In some embodiments, the antibody that binds all seven human ELR+ CXC chemokines, e.g., Antibody 1, or a pharmaceutical composition comprising such an antibody, is administered with a loading dose prior to the specified intravenous dose. For example, the loading dose can be a high intravenous dose (e.g., about 600 mg to about 1000 mg) with a shorter dosing interval (e.g., every week) for a few weeks (e.g., two, three, or four weeks). In some embodiments, the loading dose is 600 mg intravenously every week for a few weeks (e.g., two, three, or four weeks). In some embodiments, the loading dose is 700 mg intravenously every week for a few weeks (e.g., two, three, or four weeks). In some embodiments, the loading dose is 800 mg intravenously every week for a few weeks (e.g., two, three, or four weeks). In some embodiments, the loading dose is 900 mg intravenously every week for a few weeks (e.g., two, three, or four weeks). In some embodiments, the loading dose is 1000 mg intravenously every week for a few weeks (e.g., two, three, or four weeks).

As shown below, the bioavailability for subcutaneous injection of Antibody 1 is estimated to be approximately 65% of intravenous injection of Antibody 1. In some embodiments, the antibody that binds all seven human ELR+ CXC chemokines, e.g., Antibody 1, or a pharmaceutical composition comprising such an antibody, is administered subcutaneously at a dose of about 150 mg to about 1500 mg (e.g., about 150 mg to about 1500 mg, about 200 mg to about 1400 mg, about 250 mg to about 1300 mg, about 300 mg to about 1200 mg, about 350 mg to about 1100 mg, about 400 mg to about 1000 mg, about 450 mg to about 900 mg, about 600 mg to about 900 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, about 1400 mg, about 1450 mg, about 1500 mg).

In some embodiments, the antibody that binds all seven human ELR+ CXC chemokines, e.g., Antibody 1, or a pharmaceutical composition comprising such an antibody, is administered subcutaneously at a dose of about 150 mg to about 900 mg (e.g., about 150 mg to about 900 mg, about 300 mg to about 900 mg, about 450 mg to about 900 mg, about 600 mg to about 900 mg, about 750 mg to about 900 mg, about 150 mg to about 750 mg, about 300 mg to about 750 mg, about 450 mg to about 750 mg, about 600 mg to about 750 mg, about 150 mg to about 600 mg, about 300 mg to about 600 mg, about 450 mg to about 600 mg, about 150 mg to about 450 mg, about 300 mg to about 450 mg, about 150 mg to about 300 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg).

In some embodiments, the antibody that binds all seven human ELR+ CXC chemokines, e.g., Antibody 1, or a pharmaceutical composition comprising such an antibody, is administered at a dose of about 150 mg to about 900 mg (e.g., about 150 mg to about 900 mg, about 300 mg to about 900 mg, about 450 mg to about 900 mg, about 600 mg to about 900 mg, about 750 mg to about 900 mg, about 150 mg to about 750 mg, about 300 mg to about 750 mg, about 450 mg to about 750 mg, about 600 mg to about 750 mg, about 150 mg to about 600 mg, about 300 mg to about 600 mg, about 450 mg to about 600 mg, about 150 mg to about 450 mg, about 300 mg to about 450 mg, about 150 mg to about 300 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg) once every two weeks subcutaneously.

In some embodiments, the antibody that binds all seven human ELR+ CXC chemokines, e.g., Antibody 1, or a pharmaceutical composition comprising such an antibody, is administered at a dose of about 900 mg to about 1500 mg (e.g., about 900 mg to about 1500 mg, about 1000 mg to about 1400 mg, about 1100 mg to about 1300 mg, about 1000 mg, about 1100 mg, about 1200 mg, about 1300 mg, about 1400 mg, about 1500 mg) once every two weeks subcutaneously.

In some embodiments, the antibody that binds all seven human ELR+ CXC chemokines, e.g., Antibody 1, or a pharmaceutical composition comprising such an antibody, is administered at a dose of about 300 mg to about 900 mg (e.g., about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg) once every two weeks subcutaneously.

In some embodiments, the antibody that binds all seven human ELR+ CXC chemokines, e.g., Antibody 1, or a pharmaceutical composition comprising such an antibody, is administered at a dose of about 450 mg to about 900 mg (e.g., about 450 mg, about 500 mg, about 550 mg, about 600 mg, about 650 mg, about 700 mg, about 750 mg, about 800 mg, about 850 mg, about 900 mg) once every two weeks subcutaneously.

In some embodiments, the antibody that binds all seven human ELR+ CXC chemokines, e.g., Antibody 1, or a pharmaceutical composition comprising such an antibody, is administered at a dose of about 300 mg once every two weeks subcutaneously. In some embodiments, the antibody that binds all seven human ELR+ CXC chemokines, e.g., Antibody 1, or a pharmaceutical composition comprising such an antibody, is administered at a dose of about 450 mg once every two weeks subcutaneously. In some embodiments, the antibody that binds all seven human ELR+ CXC chemokines, e.g., Antibody 1, or a pharmaceutical composition comprising such an antibody, is administered at a dose of about 600 mg once every two weeks subcutaneously. In some embodiments, the antibody that binds all seven human ELR+ CXC chemokines, e.g., Antibody 1, or a pharmaceutical composition comprising such an antibody, is administered at a dose of about 900 mg once every two weeks subcutaneously.

In some embodiments, the antibody that binds all seven human ELR+ CXC chemokines, e.g., Antibody 1, or a pharmaceutical composition comprising such an antibody, is administered at a dose of about 150 mg to about 600 mg (e.g., about 150 mg to about 600 mg, about 200 mg to about 500 mg, about 250 mg to about 450 mg, about 300 mg to about 450 mg, about 350 mg to about 450 mg, about 150 mg, about 200 mg, about 250 mg, about 300 mg, about 350 mg, about 400 mg, about 450 mg, about 500 mg, about 550 mg, about 600 mg) weekly subcutaneously. In some embodiments, the antibody that binds all seven human ELR+ CXC chemokines, e.g., Antibody 1, or a pharmaceutical composition comprising such an antibody, is administered at a dose of about 250 mg to about 450 mg weekly subcutaneously. In some embodiments, the antibody that binds all seven human ELR+ CXC chemokines, e.g., Antibody 1, or a pharmaceutical composition comprising such an antibody, is administered at a dose of about 250 mg weekly subcutaneously. In some embodiments, the antibody that binds all seven human ELR+ CXC chemokines, e.g., Antibody 1, or a pharmaceutical composition comprising such an antibody, is administered at a dose of about 300 mg weekly subcutaneously. In some embodiments, the antibody that binds all seven human ELR+ CXC chemokines, e.g., Antibody 1, or a pharmaceutical composition comprising such an antibody, is administered at a dose of about 350 mg weekly subcutaneously. In some embodiments, the antibody that binds all seven human ELR+ CXC chemokines, e.g., Antibody 1, or a pharmaceutical composition comprising such an antibody, is administered at a dose of about 400 mg weekly subcutaneously. In some embodiments, the antibody that binds all seven human ELR+ CXC chemokines, e.g., Antibody 1, or a pharmaceutical composition comprising such an antibody, is administered at a dose of about 450 mg weekly subcutaneously.

In some embodiments, the antibody that binds all seven human ELR+ CXC chemokines, e.g., Antibody 1, or a pharmaceutical composition comprising such an antibody, is administered with a loading dose prior to the specified subcutaneous dose. For example, the loading dose can be a high subcutaneous dose (e.g., about 900 mg to about 1500 mg) with a shorter dosing interval (e.g., every week or every three days) for a few weeks (e.g., two, three, or four weeks) to a few months (e.g., one, two, or three months). In some embodiments, the loading dose is 900 mg subcutaneously every week for a few weeks (e.g., two, three, or four weeks) to a few months (e.g., one, two, or three months). In some embodiments, the loading dose is 1000 mg subcutaneously every week for a few weeks (e.g., two, three, or four weeks) to a few months (e.g., one, two, or three months). In some embodiments, the loading dose is 1100 mg subcutaneously every week for a few weeks (e.g., two, three, or four weeks) to a few months (e.g., one, two, or three months). In some embodiments, the loading dose is 1200 mg subcutaneously every week for a few weeks (e.g., two, three, or four weeks) to a few months (e.g., one, two, or three months). In some embodiments, the loading dose is 1300 mg subcutaneously every week for a few weeks (e.g., two, three, or four weeks) to a few months (e.g., one, two, or three months). In some embodiments, the loading dose is 1400 mg subcutaneously every week for a few weeks (e.g., two, three, or four weeks) to a few months (e.g., one, two, or three months). In some embodiments, the loading dose is 1500 mg subcutaneously every week for a few weeks (e.g., two, three, or four weeks) to a few months (e.g., one, two, or three months). In some embodiments, the loading dose is 900 mg subcutaneously every three days for a few weeks (e.g., two, three, or four weeks) to a few months (e.g., one, two, or three months). In some embodiments, the loading dose is 1000 mg subcutaneously every three days for a few weeks (e.g., two, three, or four weeks) to a few months (e.g., one, two, or three months). In some embodiments, the loading dose is 1100 mg subcutaneously every three days for a few weeks (e.g., two, three, or four weeks) to a few months (e.g., one, two, or three months). In some embodiments, the loading dose is 1200 mg subcutaneously every three days for a few weeks (e.g., two, three, or four weeks) to a few months (e.g., one, two, or three months). In some embodiments, the loading dose is 1300 mg subcutaneously every three days for a few weeks (e.g., two, three, or four weeks) to a few months (e.g., one, two, or three months). In some embodiments, the loading dose is 1400 mg subcutaneously every three days for a few weeks (e.g., two, three, or four weeks) to a few months (e.g., one, two, or three months). In some embodiments, the loading dose is 1500 mg subcutaneously every three days for a few weeks (e.g., two, three, or four weeks) to a few months (e.g., one, two, or three months). The subcutaneous loading dose can be achieved in a single injection or in a few separate injections (e.g., two, three or four injections).

In some embodiments, the antibody that binds all seven human ELR+ CXC chemokines, e.g., Antibody 1, or a pharmaceutical composition comprising such an antibody, is administered without a loading dose prior to the specified dose.

As used herein, the term "human ELR+ CXC chemokines" refers to the seven known CXC chemokines that have an E-L-R motif and that bind to CXCR1 and/or CXCR2 receptor. The human ELR+ CXC chemokines are human Gro-alpha (also known as CXCL1) (SEQ ID NO: 13), human Gro-beta (also known as CXCL2) (SEQ ID NO: 14), human Gro-gamma (also known as CXCL3) (SEQ ID NO: 15), human ENA-78 (also known as CXCL5) (SEQ ID NO: 16), human GCP-2 (also known as CXCL6) (SEQ ID NO: 17), human NAP-2 (also known as CXCL7) (SEQ ID NO: 18), and human IL-8 (also known as CXCL8) (SEQ ID NO: 19). Collectively, all seven human ELR+ CXC chemokines are called "human pan-ELR+ CXC chemokines" herein.

The term "antibody," as used herein, refers to monoclonal immunoglobulin molecules comprising four polypeptide chains, two heavy (H) chains and two light (L) chains inter-connected by disulfide bonds. Each heavy chain comprises a heavy chain variable region (HCVR) and a heavy chain constant region. The heavy chain constant region comprises three domains, CH1, CH2, and CH3. Each light chain is comprised of a light chain variable region (LCVR) and a light chain constant region, CL. The HCVR and LCVR regions can be further subdivided into regions of hypervariability, termed complementarity determining regions (CDRs), interspersed with regions that are more conserved, termed framework regions (FR). Each HCVR and LCVR is composed of three CDRs and four FRs, arranged from amino-terminus to carboxyl-terminus in the following order: FR1, CDR1, FR2, CDR2, FR3, CDR3, FR4. The CDR regions in HCVR are termed HCDR1, HCDR2, and HCDR3. The CDR regions in LCVR are termed LCDR1, LCDR2, and LCDR3. The CDRs contain most of the residues which form specific interactions with the antigen. There are currently three systems of CDR assignments for antibodies that are used for sequence delineation. The Kabat CDR definition (Kabat et al., "Sequences of Proteins of Immunological Interest," National Institutes of Health, Bethesda, Md. (1991)) is based upon antibody sequence variability. The Chothia CDR definition (Chothia et al., "Canonical structures for the hypervariable regions of immunoglobulins", Journal of Molecular Biology, 196, 901-

917 (1987); Al-Lazikani et al., "Standard conformations for the canonical structures of immunoglobulins", Journal of Molecular Biology, 273, 927-948 (1997)) is based on three-dimensional structures of antibodies and topologies of the CDR loops. The Chothia CDR definitions are identical to the Kabat CDR definitions with the exception of HCDR1 and HCDR2. For the purposes of the present invention, a hybrid of the Kabat and Chothia definitions are used to define CDRs. The assignment of amino acids in the HCVR and LCVR regions is in accordance with the Kabat numbering convention. It is further understood that the term "antibody" encompasses any cellular post-translational modifications to the antibody including, but not limited to, acylation and glycosylation.

As used herein, the term "septa-specific antibody" refers to an antibody that binds all seven human ELR+ CXC chemokines with high affinity (e.g., with binding affinity ($K_D$) in the range of from about $5 \times 10^{-11}$ M to about $1 \times 10^{-9}$ M).

As used herein, a "patient" refers to a human with a disease, disorder, or condition that would benefit from a decreased level of human ELR+ CXC chemokines or decreased bioactivity induced by human ELR+ CXC chemokines.

As used herein, "treatment" or "treating" refers to all processes wherein there may be a slowing, controlling, or stopping of the progression of the disorders disclosed herein, but does not necessarily indicate a total elimination of all disorder symptoms. Treatment includes administration of an antibody of the present invention for treatment of a disease or condition in a patient, particularly in a human.

A SINGLE-ASCENDING DOSE STUDY TO EVALUATE THE SAFETY, TOLERABILITY, PHARMACOKINETICS, AND PHARMACODYNAMICS OF ANTIBODY 1 IN HEALTHY SUBJECTS (NCT02148627)

The primary objective of this study is to explore the safety and tolerability of a single dose of Antibody 1 in healthy subjects, including Japanese subjects, in order to define an appropriate dose range for further clinical research. The endpoints for this objective are incidence of SAEs (serious adverse events) and TEAEs (treatment-emergent adverse events). The secondary objective of this study is to characterize the pharmacokinetics (PK) of Antibody 1, including estimation of the bioavailability following subcutaneous (SC) administration of a single dose of Antibody 1, in healthy subjects, including Japanese subjects. The endpoints include Cmax (maximum observed drug concentration), tmax (time to reach Cmax), AUCs (area under the concentration-time curve during dosing interval at steady) and the presence of antidrug antibodies.

In this study, Antibody 1 has been administered to 39 healthy subjects in a single-ascending dose study in which doses of 10 mg, 30 mg, 100 mg, 200 mg, 400 mg, or 700 mg of Antibody 1 were administered as a slow intravenous (IV) infusion; or the dose of 100 mg of Antibody 1 was administered by SC injection to assess the bioavailability. In addition, skin blisters were induced in subjects who received IV doses of 10 mg, 30 mg, 100 mg, 200 mg, and 400 mg of Antibody 1 to assess neutrophil chemotaxis and accumulation.

There were no deaths or serious adverse events (SAEs) reported. Adverse events (AEs) reported were graded using the Common Terminology Criteria for Adverse Events (CT-CAE). All AEs reported were Grade 1, except for 1 subject who reported a Grade 2 event, which the investigator considered to be unrelated to study drug.

There were no clinically significant changes in hematology (including peripheral blood neutrophil counts) or urinalysis.

There were no clinically significant changes in vital signs or electrocardiograms (ECG).

Antibody 1 exhibited linear PK in the dose range tested, with an estimated terminal half-life (t½) of approximately 2 weeks. The estimated bioavailability for SC injection of Antibody 1 is approximately 65% of IV injection.

The preliminary pharmacodynamic (PD) assessment was focused on the percentage of neutrophils present in the blister fluid. The neutrophil data were highly variable, but a trend of dose-dependent decreases of neutrophils in the blister fluid was observed. A Multiple-Dose, Dose-Escalation Study to Evaluate the Safety, Tolerability, and Pharmacokinetics of Antibody 1 in Patients with Skin Diseases (NCT02896868)

The primary objective is to assess the safety and tolerability of multiple intravenous doses of Antibody 1 in patients with skin disease, e.g., hidradenitis suppurativa. The endpoints for this objective are incidence of SAEs (serious adverse events) and TEAEs (treatment-emergent adverse events).

The secondary objectives are to estimate the PK parameters of Antibody 1 following IV administration in patients with skin disease, e.g., HS; and to assess the potential development of antidrug antibodies and their impact on safety and PK of Antibody 1. The endpoints include Cmax (maximum observed drug concentration), tmax (time to reach Cmax), AUCs (area under the concentration-time curve during dosing interval at steady) and the presence of antidrug antibodies.

The exploratory objectives are to explore the dose- and exposure-response relationship for appropriate clinical endpoints for the dermatological condition and other PD measures (e.g., clinical rating scores). The endpoints include HiSCR, abscess and inflammatory nodule counts, modified Sartorius score, HS-PGA score, and Patient's Global Assessment of Skin Pain (via Numeric Rating Scale).

This is a multicenter, randomized, placebo-controlled, and multiple ascending dose study in patients with skin disease, e.g., HS. The patient and investigator are blinded to study treatment. Screening occurs up to 28 days prior to the first dose of Antibody 1.

Patients participating in the study receive a slow IV infusion over a minimum period of 30 minutes, or longer after completion of the infusion, at the investigator's discretion. Antibody 1 or placebo is administered every 2 weeks (Q2W) for a total of 4 doses. The Q2W dosing frequency is selected because the t½ of Antibody 1 is approximately 2 weeks. The dose levels for patients with HS are 300 mg and 600 mg of Antibody 1, which are selected based on the NCT02148627 study.

Samples for PK analysis are taken prior to each infusion, at the end of the first infusion, and for 12 weeks after the final dose. Clinical laboratory safety tests, vital signs, and ECGs are assessed throughout the dosing period, and for 12 weeks after the final dose. Immunogenicity (antidrug antibodies) are assessed at multiple time points, with the final sample being taken 12 weeks after the last infusion of study medication.

Eligibility of patients for study enrollment is based on the results of screening medical history, physical examination (including weight, height, and temperature), vital signs, clinical laboratory tests, and ECGs.

The nature of any conditions present at the time of the physical examination and any preexisting conditions or relevant medical history are documented.

Screening may occur up to 28 days prior to enrollment. Patients who are not enrolled within 28 days of screening may be subjected to an additional medical assessment and/or clinical measurements to confirm their eligibility. Some tests may be repeated, at the discretion of the investigator, and do not constitute "rescreening".

Patients are eligible for inclusion in the study only if they meet all of the following criteria at screening and/or enrollment:

[1] suffer from chronic Hidradenitis Suppurativa, and have a diagnosis of HS for at least 1 year prior to baseline and have received previous antibiotic therapy and meet the following criteria:
  have presence of HS lesions in at least 2 distinct anatomical areas, one of which must be at least Hurley Stage II or Hurley Stage III;
  have Hidradenitis Suppurativa-Physician Global Assessment (HS-PGA) score of at least moderate severity at Visit 2 with at least 3 abscesses and/or nodules;
  have experienced an inadequate response to oral antibiotics for treatment of HS;
[2] are at least 18 years of age;
  male patients: agree to use an effective method of contraception and should not donate sperm for the duration of the study plus 3 months following the last dose of Antibody 1;
  female patients: women not of childbearing potential may participate, and include those who are infertile or postmenopausal;
  female patients: women of childbearing potential who test negative for pregnancy prior to each dose of treatment based on a urine pregnancy test may participate. They must agree to use 1 highly effective method of contraception or a combination of 2 effective methods of contraception during the study and for 3 months following the last dose of Antibody 1;
[3] have a minimum body weight of 50 kg at screening;
[4] have venous access sufficient to allow for blood sampling and administration of Antibody 1, as per the protocol;
[5] are reliable and willing to make themselves available for the duration of the study, and are willing to follow study procedures;
[6] are able and willing to give signed informed consent;
[7] have adequate organ function, including at screening:
  hematologic: absolute neutrophil count $\geq 1.8 \times 10^9/L$, platelet count $\geq 100 \times 10^9/L$, hemoglobin level $\geq 10.0$ g/dL, absolute lymphocyte count $>0.8 \times 10^9/L$ (patients $\geq 60$ years of age) or $1.0 \times 10^9/L$ (patients $\leq 59$ years of age), and total white blood cell count $\geq 3 \times 10^9/L$
  hepatic: bilirubin level $\leq 1.5 \times$ the ULN (upper limit of normal) and alkaline phosphatase (ALP), alanine aminotransferase (ALT), and aspartate aminotransferase (AST)$\leq 1.5 \times$ULN
  renal: serum creatinine level $\leq 1.5 \times$ULN.

Exclusion criteria include:
within 14 days prior to Day 1 of study (Visit 2), have received oral opioids for HS-related pain, or are anticipated to take these during the study;
have presence of more than 25 draining fistulae;
have had surgical treatment for HS in the last 4 weeks prior to first dose of Antibody 1;
are study site personnel directly affiliated with this study or their immediate families. Immediate family is defined as a spouse, biological or legal guardian, child, or sibling;
are Sponsor employees and alliance partners involved with the study who require exclusion of their employees;
are currently enrolled in a clinical trial involving an Investigator Product (IP) or any other type of medical research judged not to be scientifically or medically compatible with this study;
have participated, within the last 30 days (at Visit 2) in a clinical trial involving an IP. If the previous IP has a half-life of greater than 7 days, 3 months, or 5 half-lives (whichever is longer) should have passed;
have previously completed or withdrawn from this study or any other study investigating Antibody 1, and have previously received Antibody 1;
have known allergies to Antibody 1, related compounds, or any components of the formulation, or history of significant atopy;
have an abnormality in the 12-lead ECG that, in the opinion of the investigator, increases the risks associated with participating in the study;
have an abnormal blood pressure, as determined by the investigator;
have significant history of or current cardiovascular, respiratory, hepatic, renal, gastrointestinal, endocrine, hematological, or neurological disorders capable of significantly altering the absorption, metabolism, or elimination of drugs; of constituting a risk when taking the IP; or of interfering with the interpretation of data;
have past history of significant neuropsychiatric disorders (including, but not limited to, suicidal ideation, attempted suicide, bipolar disorder, and prolonged depression) or clinically significant ongoing neuropsychiatric disorders;
regularly use known drugs of abuse and/or show positive findings on urinary drug screening;
show evidence of human immunodeficiency virus (HIV) infection and/or positive human HIV antibodies;
show evidence of hepatitis C and/or positive hepatitis C antibody;
show evidence of hepatitis B: positive for hepatitis B core antibody (HBcAb+) and/or positive hepatitis B surface antigen;
have received any systemic (including oral) antibiotic or anti-infective treatment within 28 days prior to baseline;
at the investigator's discretion, have any significant infection within 28 days of screening, or have evidence of active infection within 14 days prior to first dose;
in the opinion of the investigator, are at risk of septicemia;
are women who are lactating;
have donated blood of more than 500 mL within the last month (at screening visit);
have an average weekly alcohol intake that exceeds 21 units per week (male patients up to age 65) and 14 units per week (male patients over 65 and female patients); where 1 unit=12 oz or 360 mL of beer, 5 oz or 150 mL of wine, 1.5 oz or 45 mL of distilled spirits;
have had symptomatic herpes zoster within 3 months of screening;

show evidence of active or latent tuberculosis (TB), as documented by medical history and examination, chest x-rays (posterior-anterior and lateral), and TB testing: either a negative tuberculin skin test defined as a skin induration <5 mm at 48 to 72 hours, or a negative (not indeterminate) QuantiFERON®-TB Gold test. The choice to perform a tuberculin skin test or a QuantiFERON-TB Gold test is made by the investigator, according to local licensing and standard of care, but should be used for patients who have previously received the *Bacillus* Calmette-Guerin vaccine. The QuantiFERON-TB Gold test can only be used in countries where it is licensed, and the use of this test is dependent on previous treatment(s). This test may not be suitable if previous treatment(s) produce significant immunosuppression;

have received attenuated live vaccine(s) within 1 month of screening, or intend to during the study are immunocompromised;

have received treatment with biologic agents (such as monoclonal antibodies, including marketed drugs) within 3 months or 5 half-lives (whichever is longer), prior to baseline. Patients who have previously received biologics for the indication of interest and have failed due to lack of primary efficacy are excluded from participation in this study;

have significant allergies to humanized monoclonal antibodies;

have clinically significant multiple or severe drug allergies, or intolerance to topical corticosteroids, or severe posttreatment hypersensitivity reactions (including, but not limited to, erythema multiforme major, linear immunoglobulin [Ig] A dermatosis, toxic epidermal necrolysis, or exfoliative dermatitis);

have had lymphoma, leukemia, or any malignancy within the past 5 years, except for basal cell or squamous epithelial carcinomas of the skin that have been resected, with no evidence of metastatic disease for 3 years;

have had breast cancer within the past 10 years;

in the opinion of the investigator or sponsor, are unsuitable for inclusion in the study.

Results:

Four HS patients have been intravenously dosed with 300 mg of Antibody 1 every 2 weeks (Q2W) for a total of 4 doses; and one HS patient received placebo with the same dose and dosing regimen. After 8 weeks of treatment (2 weeks after the last dose), three of the four HS patients dosed with 300 mg of Antibody 1 observed a >=50% reduction in their counts of abscesses and inflammatory nodules, with one of the four HS patients meeting all of the criteria for the Hidradenitis Suppurativa Clinical Response (HiSCR) endpoint.

Three HS patients have been intravenously dosed with 600 mg of Antibody 1 every 2 weeks (Q2W) for a total of 4 doses. After 8 weeks of treatment (2 weeks after the last dose), all three HS patients dosed with 600 mg of Antibody 1 observed a >=50% reduction in their counts of abscesses and inflammatory nodules, and all three patients met all of the criteria for the HiSCR endpoint.

There have been no deaths, SAEs, or discontinuations due to AEs observed in this study.

Therefore, Antibody 1 can be used to safely and effectively treat hidradenitis suppurativa in human patients.

Sequences
Antibody 1 Heavy chain amino acid sequence:
SEQ ID NO: 1
QVQLVQSGAEVKKPGASVKVSCKASGYEFTSYWIHWVRQAPGQGLEW

MGNISPNSGSANYNEKFKSRVTMTRDTSTSTVYMELSSLRSEDT AV

YYCAREGPYSYYPSREYYGSDLWGQGTL VTVSSASTKGPSVFPLAP

CSRSTSEST AALGCLVKDYFPEPVTVSWNSGALTSGVHTFP AVLQ

SSGLYSLSSVVTVPSSSLGTKTYTCNVDHKPSNTKVDKRVESKYGPP

CPPCPAPEFLGGPSVFLFPPKPKDTLMISRTPEVTCVVVDVSQEDPE

VQFNWYVDGVEVHNAKTKPREEQFNSTYRVVSVLTVLHQDWLNGKEY

KCKVSNKGLPSSIEKTISKAKGQPREPQVYTLPPSQEEMTKNQVSLT

CL VKGFYPSDIAVEWESNGQPENNYKTTPPVLDSDGSFFL YSRLT

VDKSRWQEGNVFSCSVMHEALHNHYTQKSLSLSLG

Antibody 1 Heavy chain variable region:
SEQ ID NO: 2
QVQLVQSGAEVKKPGASVKVSCKASGYEFTSYWIHWVRQAPGQGLEW

MGNISPNSGSANYNEKFKSRVTMTRDTSTSTVYMELSSLRSEDT AV

YYCAREGPYSYYPSREYYGSDLWGQGTLVTVSS

Antibody 1 Light chain amino acid sequence:
SEQ ID NO: 3
EIVLTQSPA TLSLSPGERATLSCRASQSISNNLHWYQQKPGQAPRL

LIYYTSRSVSGIPARFSGSGSGTDFTL TISSLEPEDFA VYYCGQN

NEWPEVFGGGTKVEIKRTV AAPSVFIFPPSDEQLKSGT ASVVCLL

NNFYPREAKVQWKVDNALQSGNSQESVTEQDSKDSTYSLSSTLTLSK

ADYEKHKVY ACEVTHQGLSSPVTKSFNRGEC

Antibody 1 Light chain variable region:
SEQ ID NO: 4
EIVLTQSPATLSLSPGERATLSCRASQSISNNLHWYQQKPGQAPRLL

IYYTSRSVSGIPARFSGSGSGTDFTL TISSLEPEDFA VYYCGQNN

EWPEVFGGGTKVEIK

Antibody 1 Heavy chain DNA sequence:
SEQ ID NO: 5
CAGGTGCAGCTGGTGCAGTCTGGTGCTGAAGTGAAGAAGCCTGGGGC

CTCAGTGAAGGTGTCCTGCAAGGCATCTGGCTACGAGTTCACCAGCT

ACTGGATTCACTGGGTGCGACAGGCCCCTGGACAAGGGCTTGAGTGG

ATGGGAAATATTTCTCCTAATAGTGGTAGTGCTAACTACAATGAGAA

GTTCAAGAGCAGAGTCACCATGACCAGGGACACGTCCACGAGCACAG

TCTACATGGAGCTGAGCAGCCTGAGATCTGAGGACACGGCCGTGTAT

TACTGTGCGAGAGAGGGCCCTTACAGTTATTATCCGAGTAGGGAGTA

CTATGGCTCTGACCTCTGGGGCAAGGGACCCTAGTCACAGTCTCCT

CAGCCTCCACCAAGGGCCCATCGGTCTTCCCGCTAGCGCCCTGCTCC

AGGAGCACCTCCGAGAGCACAGCCGCCCTGGGCTGCCTGGTCAAGGA

CTACTTCCCCGAACCGGTGACGGTGTCGTGGAACTCAGGCGCCCTGA

CCAGCGGCGTGCACACCTTCCCGGCTGTCCTACAGTCCTCAGGACTC

TACTCCCTCAGCAGCGTGGTGACCGTGCCCTCCAGCAGCTTGGGCAC

GAAGACCTACACCTGCAACGTAGATCACAAGCCCAGCAACACCAAGG

-continued

TGGACAAGAGAGTTGAGTCCAAATATGGTCCCCCATGCCCACCCTGC

CCAGCACCTGAGTTCCTGGGGGGACCATCAGTCTTCCTGTTCCCCCC

AAAACCCAAGGACAC TCTCATGATCTCCCGGACCCCTGAGGTCACG

TGCGTGGTGGTGGACGTGAGCCAGGAAGACCCCGAGGT CCAGTTCA

ACTGGTACGTGGATGGCGTGGAGGTGCATAATGCCAAGACAAAGCCG

CGGGAGGAGCAGTTCAACAGCACGTACCGTGTGGTCAGCGTCCTCAC

CGTCCTGCACCAGGACTGGCTGAACGGCAAGGAGTACAAGT GCAAG

GTCTCCAACAAAGGCCTCCCGTCCTCCATCGAGAAAACCATCTCCAA

AGCCAAAGGGCAGCCCCGAGAGCCACAGGT GTACACCCTGCCCCCA

TCCCAGGAGGAGAT GACCAAGAACCAGGTCAGCCTGACCTGCCTGG

TCAAAGGCTTCTACCCCAGCGACATCGCCGTGGAGTGGGAAAGCAAT

GGGCAGCCGGAGAACAAC TACAAGACCACGCCTCCCGTGCTGGACT

CCGACGGCTCCTTCTTCCTCTACAGCAGGCTAACCGTGGACAAGAGC

AGGTGGCAGGAGGGGAATGTCTTCTCATGCTCCGTGATGCATGAGGC

TCTGCACAACCACTACACACAGAAGAGCC TCTCCCTGTCTCTGGGT

Antibody 1 Light chain DNA sequence:
SEQ ID NO: 6

GAAATTGTGTTGACACAGTCTCCAGCCACCCTGTCTTTGTCTCCAGG

GGAAAGAGCCACCCTCTCCTGCAGGGCCAGTCAAAGTATCAGCAATA

ACCTACACTGGTACCAACAGAAACC TGGCCAGGCTCCCAGGCTCCT

CATCTATTATACTTCCCGGTCCGTCTCTGGCATCCCAGCCAGGTTCA

GTGGCAGTGGGTCTGGGACAGACTTCACTCTCACCATCAGCAGCCTA

GAGCCTGAAGATTTTGCAGTTTATTACTGTGGACAGAATAACGAGTG

GCCTGAGGTGTTCGGCGGAGGGACCAAGGTGGAGATCAAACGAACTG

TGGCTGCACCATCTGTCTTCATCTTCCCGCCATCTGATGAGCAGTTG

AAATCTGGAACTGCCTCTGTTGTGTGCCTGCTGAATAACTTCTATCC

CAGAGAGGCCAAAGTACAGT GGAAGGTGGATAACGCCCTCCAATCG

GGTAACTCCCAGGAGAGTGTCACAGAGCAGGACAGCAAGGACAGCAC

CTACAGCCTCAGCAGCACCCTGACGCTGAGCAAAGCAGACTACGAGA

AACACAAAGTCTACGCCTGCGAAGTCACCCATCAGGGCCTGAGCTCG

CCCGTCACAAAGAGCTTCAACAGGGGAGAGTGC

Antibody 1 LCDR1:
SEQ ID NO: 7
RASQSISNNLH

Antibody 1 LCDR2:
SEQ ID NO: 8
YTSRSVS

Antibody 1 LCDR3:
SEQ ID NO: 9
GQNNEWPEV

Antibody 1 HCDR1:
SEQ ID NO: 10
GYEFTSYWIH

Antibody 1 HCDR2:
SEQ ID NO: 11
NISPNSGSANYNEKFKS

Antibody 1 HCDR3:
SEQ ID NO: 12
EGPYSYYPSREYYGSDL

Human Gro-alpha (CXCL1):
SEQ ID NO: 13
ASVATELRCQCLQTLQGIHPKNIQSVNVKSPGPHCAQTEVIATLKNG
RKACLNPASPIVKKIIEKMLNSDKSN Human Gro-beta (CXCL2):
SEQ ID NO: 14
APLATELRCQCLQTLQGIHLKNIQSVKVKSPGPHCAQTEVIATLKNG
QKACLNPASPMVKKIIEKMLKNGKSN Human Gro-gamma (CXCL3):
SEQ ID NO: 15
ASVVTELRCQCLQTLQGIHLKNIQSVNVRSPGPHCAQTEVIATLKNG
KKACLNPASPMVQKIIEKILNKGSTN Human ENA-78 (CXCL5):
SEQ ID NO: 16
AAVLRELRCVCLQTTQGVHPKMISNLQVFAIGPQCSKVEVVASLKNG
KEICLDPEAPFLKKVIQKILDGGNKEN Human GCP-2 (CXCL6):
SEQ ID NO: 17
VSAVLTELRCTCLRVTLRVNPKTIGKLQVFPAGPQCSKVEVVASLKN
GKQVCLDPEAPFLKKVIQKILDSGNKKN Human NAP-2 (CXCL7):
SEQ ID NO: 18
AELRCMCIKTTSGIHPKNIQSLEVIGKGTHCNQVEVIATLKDGRKIC
LDPDAPRIKKIVQKKLAGDESAD Human IL-8 (CXCL8):
SEQ ID NO: 19
SAKELRCQCIKTYSKPFHPKFIKELRVIESGPHCANTEIIVKLSDGR
ELCLDPKENWVQRVVEKFLKRAENS

---

The invention claimed is:

1. A method of treating hidradenitis suppurativa in a human patient in need thereof, comprising administering to the human patient a therapeutically effective amount of an antibody that binds human growth-regulated oncogene ("Gro")-alpha, human Gro-beta, human Gro-gamma, human epithelial neutrophil activating peptide-78, human granulocyte chemotactic protein-2, human neutrophil activating protein-2, and human interleukin-8, wherein the antibody comprises light chain complementarity determining regions ("LCDR") LCDR1, LCDR2, LCDR3, and heavy chain complementarity determining regions ("HCDR") HCDR1, HCDR2, HCDR3, wherein LCDR1 comprises SEQ ID NO: 7, LCDR2 comprises SEQ ID NO: 8, LCDR3 comprises SEQ ID NO: 9, HCDR1 comprises SEQ ID NO: 10, HCDR2 comprises SEQ ID NO: 11, and HCDR3 comprises SEQ ID NO: 12.

2. The method of claim 1, wherein the antibody comprises a heavy chain variable region comprising the amino acid sequence of SEQ ID NO: 2 and a light chain variable region comprising the amino acid sequence of SEQ ID NO: 4.

3. The method of claim 1, wherein the antibody comprises a heavy chain having the amino acid sequence of SEQ ID NO: 1 and a light chain having the amino acid sequence of SEQ ID NO: 3.

4. The method of claim 1, wherein the antibody is administered at a dose of about 100 mg to about 1000 mg intravenously.

5. The method of claim 1, wherein the antibody is administered at a dose of about 150 mg to about 1500 mg subcutaneously.

6. The method of claim 1, wherein the antibody is administered once every two weeks.

7. The method of claim 1, wherein the antibody is administered at a dose of about 100 mg to about 600 mg once every two weeks intravenously.

8. The method of claim 1, wherein the antibody is administered at a dose of about 300 mg to about 600 mg once every two weeks intravenously.

9. The method of claim 1, wherein the antibody is administered at a dose of about 100 mg to about 150 mg once every two weeks intravenously.

10. The method of claim 1, wherein the antibody is administered at a dose of about 300 mg once every two weeks intravenously.

11. The method of claim 1, wherein the antibody is administered at a dose of about 600 mg once every two weeks intravenously.

12. The method of claim 7, further comprising administering a loading dose of the antibody.

13. The method of claim 12, wherein the loading dose is about 600 mg to about 1000 mg intravenously every week for three weeks.

14. The method of claim 1, wherein the antibody is administered at a dose of about 150 mg to about 900 mg once every two weeks subcutaneously.

15. The method of claim 1, wherein the antibody is administered at a dose of about 450 mg to about 900 mg once every two weeks subcutaneously.

16. The method of claim 1, wherein the antibody is administered at a dose of about 300 mg once every two weeks subcutaneously.

17. The method of claim 1, wherein the antibody is administered at a dose of about 450 mg once every two weeks subcutaneously.

18. The method of claim 1, wherein the antibody is administered at a dose of about 600 mg once every two weeks subcutaneously.

19. The method of claim 1, wherein the antibody is administered at a dose of about 900 mg once every two weeks subcutaneously.

20. The method of claim 1, wherein the antibody is administered at a dose of about 250 mg to about 450 mg weekly subcutaneously.

21. The method of claim 14, further comprising administering a loading dose of the antibody.

22. The method of claim 21, wherein the loading dose is about 900 mg to about 1500 mg subcutaneously every week or every three days for three weeks.

* * * * *